United States Patent [19]

Wong et al.

[11] Patent Number: 5,019,397

[45] Date of Patent: May 28, 1991

[54] AQUEOUS EMULSION FOR PHARMACEUTICAL DOSAGE FORM

[75] Inventors: Patrick S. L. Wong, Hayward; Felix Theeuwes, Los Altos, both of Calif.

[73] Assignee: Alza Corporation, Palo Alto, Calif.

[21] Appl. No.: 184,478

[22] Filed: Apr. 21, 1988

[51] Int. Cl.$^5$ .............................................. A61K 9/24
[52] U.S. Cl. ...................................................... 424/473
[58] Field of Search ............... 424/473, 464, 484, 485, 424/486, 488

[56] References Cited

U.S. PATENT DOCUMENTS

| | | | |
|---|---|---|---|
| 3,207,824 | 9/1965 | Wurster et al. ...................... | 264/117 |
| 3,845,770 | 11/1974 | Theeuwes et al. ................... | 128/260 |
| 3,865,108 | 2/1975 | Hartop ................................. | 128/260 |
| 3,916,899 | 11/1975 | Theeuwes et al. ................... | 128/260 |
| 4,002,173 | 1/1977 | Manning et al. ..................... | 128/296 |
| 4,063,064 | 12/1977 | Saunders et al. .................... | 219/121 |
| 4,088,864 | 5/1978 | Theeuwes et al. ................... | 219/121 |
| 4,177,177 | 12/1979 | Vanderhoff et al. ................. | 260/292 M |
| 4,200,098 | 4/1980 | Ayer et al. ........................... | 128/260 |
| 4,207,893 | 6/1980 | Michaels ............................. | 128/260 |
| 4,285,987 | 8/1981 | Ayer et al. ........................... | 427/3 |
| 4,327,725 | 5/1982 | Cortese et al. ...................... | 128/260 |
| 4,857,336 | 8/1989 | Khanna ............................... | 424/473 |

*Primary Examiner*—Merrell C. Cashion, Jr.
*Assistant Examiner*—Tim R. Horne
*Attorney, Agent, or Firm*—Paul L. Sabatine; Edward L. Mandell; Steven F. Stone

[57] ABSTRACT

A dosage form is disclosed comprising a cured emulsion that coat that surrounds a drug. The emulsion comprises a lower alkyl acrylate-lower alkyl methacrylate copolymer and ethyl cellulose. The emulsion optionally comprises a hydrophilic polymer.

4 Claims, 1 Drawing Sheet

AQUEOUS EMULSION FOR PHARMACEUTICAL DOSAGE FORM

FIELD OF THE INVENTION

This invention pertains to a pharmaceutical dosage form comprising an aqueous emulsion coat and to an aqueous emulsion coat.

BACKGROUND OF THE INVENTION

In Remington's *Pharmaceutical Sciences*, 14th Ed., p 1681, (1970), it is reported that pill coating has been a pharmaceutically accepted technique for well over ten centuries. For instance, Rhazes (850–932 A. D.) in the ninth century used a mucilage for coating pills, and Avicenna (980–1037 A. D.) is credited with the introduction of silver and gold pill coatings into medicine. At one time the coating of pills with finely powdered talcum, called pearl coating, was very popular. The gelatin coating of pills was introduced by Garot in 1838. The first sugar coated pills in the United States were imported from France in about 1842. The first sugar coated pills manufactured in the United States was in 1856 by Warner, a Philadelphia pharmacist. The coating of pills with tolu was done in about 1860 and twenty-four years later Unna introduced the enteric coated pill.

Various pharmaceutical articles of manufacture have been coated by the drug dispensing art. For example, tablets were coated to provide a more attractive dosage form, to protect the drug content from moisture and to enhance its taste. Then too, tablets were provided with a coat for releasing a drug by enteric dissolution in the intestine of a warm-blooded animal. Recently, in 1972, Theeuwes and Higuchi coated osmotic dosage forms with a semipermeable rate controlling wall for delivering a drug at a known rate per unit time.

While the above-mentioned dosage forms are useful in the management of health and disease serious disadvantages are associated with them. That is, usually organic solvents are used for applying the coating to the drug and serious, unwanted drawbacks accompany the use of organic solvents. For example, organic solvents generally are toxic to living tissue and they must be substantially pulled from the dosage form to avoid a hazard to the dosage form's recipient. Another serious drawback with the use of organic solvents is that they are flammable thereby possibly providing the danger of fire during the manufacturing process. Also, organic solvents present an environmental problem and the use of such solvents requires complicated recovery systems to avoid contaminating the environment. The recovery systems are expensive to operate and adds to the cost of the final dosage form.

It will be appreciated by those skilled in the drug dispensing art that if a coating is provided that is substantially free of organic solvents when coating drugs, drug granules, drug powders, drug dispensers, and the like, such a coating would have an immediate positive value and, concomitantly, represent an advancement in the drug coating art. Likewise, it will be appreciated by those versed in the dispensing art that if a coating that is applied from a non-organic solvent, and the coated delivery device possesses the thermodynamic ability to deliver a beneficial drug at a controlled rate, such a delivery device would have a practical application in the field of human and veterinary medicine.

OBJECTS OF THE INVENTION

In view of the above presentation it is an immediate object of this invention to provide a novel and useful coating composition for dosage forms, which coating composition overcomes the disadvantages associated with the prior art.

Another object of this invention is to provide a new coating composition comprising pharmaceutically acceptable ingredients, and which coating composition is innocuous and useful for manufacturing dosage forms.

Another object of this invention is to provide a non-toxic coating composition that is substantially free of organic solvents, and which coating composition is useful for making dosage forms by standard manufacturing techniques.

Another object of this invention is to provide a aqueous based coating composition, which composition is relatively uncomplicated, is capable of application without difficulty, and has a relatively low cost.

Another object of the invention is to provide an aqueous polymeric coating composition that exhibits long term stability and is resistant to sedimentation in a fluid environment of use.

Another object of this invention is to provide an aqueous coating composition that is useful for manufacturing a drug delivery device possessing drug release rate controlling properties.

Another object of this invention is to provide a drug delivery device that can be manufactured by conventional manufacturing procedures into various sizes, shapes and designs that comprise an improvement in the dispensing art characterized by coating the device with a non-toxic, aqueous coat that surrounds a drug.

Another object of this invention is to provide an aqueous-solvent coating composition that is nonflammable, is not an environmental hazard during formulation and when applied to a drug core.

Another object of this invention is to provide a process for applying an aqueous coating onto a drug core thereby providing an orally administrable drug dosage form.

Other objects, features and advantages of this invention will be more apparent to those versed in the drug dispensing art from the following detailed specification taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows.

In the drawings and in the specification like parts in related figures are identified by like number. The terms appearing earlier in the description of the drawings, as well as embodiments thereof, are further described elsewhere in the disclosure.

DETAILED DESCRIPTION OF THE DRAWINGS

Figure 1:
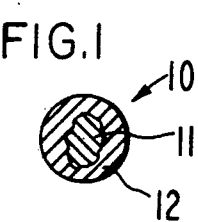
FIG. 1 is an opened view depicting a powdered drug coated with the coating composition provided by this invention.

Turning now to the drawing figures in detail, which figures are examples of dosage forms comprising a coating composition provided by this invention, and which examples are not to be considered as limiting the invention, one example of a dosage form is illustrated in FIG. 1. In FIG. 1 a dosage form 10 comprises a powdered drug 11, generally exhibiting a powder size that passes through a sieve having an opening from 0.074 mm to 0.250 mm, surrounded by a coating composition 12. Coating composition 12 comprises an aqueous emulsion of ethylacrylatemethyl methacrylate and an aqueous latex of ethylcellulose. Coating composition 12 optionally comprises a hydrophilic polymer such as polyvinyl alcohol, and the like.

Figure 2:
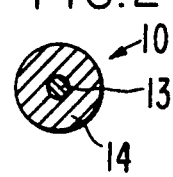
FIG. 2 is an opened view illustrating granules of a beneficial drug coated with the aqueous-carrier based composition provided by this invention.

In FIG. 2 another embodiment of dosage form 10 is seen in opened view. In FIG. 2 dosage form 10 comprises granules 13 of drug. The drug granules generally exhibit a granule size that passes through a sieve having an opening from greater than 0.250 mm to 9.50 mm. Drug granules 13 are surrounded by aqueous applied coating composition 14. Coating composition 14, in a presently preferred embodiment, comprises an aqueous emulsion of an acrylate-methacrylate polymer exhibiting a glass transition temperature of about 10° C., an aqueous latex that is partially miscible with the aqueous emulsion of the acrylate and which latex imports mechanical stability to the acrylate emulsion, and an optional hydrophilic polymer that regulates the water permeability of the aqueous acrylate-latex composition. The wall, or the membrane composition, is formed by coalescence of the latex particles that are intermingled with the water soluble polymer during a low temperature curing cycle. In a presently preferred embodiment at least one component of the ingredients comprising the blended emulsion exhibits a glass transition temperature lower than the curing temperature so that coalescence occurs during the drying period.

Figure 3:
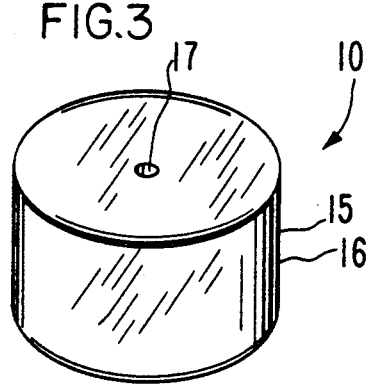
FIG. 3 is a view of an osmotic device designed and shaped for orally administering a dosage amount of a drug to the gastrointestinal tract of a warm-blooded animal.

In FIG. 3 another embodiment of dosage form 10 is illustrated manufactured as an osmotic drug delivery device 10. In FIG. 3 osmotic dosage form 10 comprises a body 15 comprising a wall 16 that surrounds and forms an internal compartment, not seen in FIG. 3. Osmotic dosage form 10 comprises at least one passageway 17 for connecting the interior of dosage form 10 with the exterior of osmotic dosage form 10.

Figure 4:
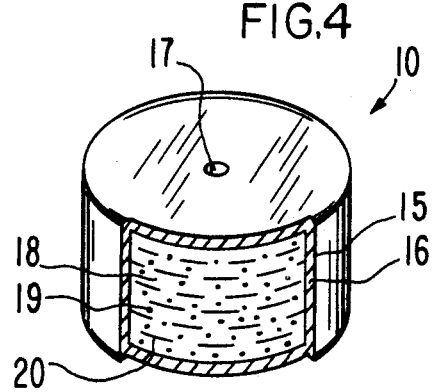
FIG. 4 is an opened view of the osmotic device of FIG. 3 depicting the wall of the osmotic device comprising a wall-forming coating composition provided by the invention.

In FIG. 4 osmotic dosage form 10 is seen in opened section. In FIG. 4 osmotic dosage form 10 comprises body member 15, aqueous applied coat wall 16, and exit passageway 17. Wall 16 surrounds and forms an internal compartment 18. Internal compartment 18 comprises a dispensable drug 19 identified by dots, and an optional osmagent 20 represented by dashes. Wall 16 is permeable to the passage of an exterior fluid present in the environment of use, and wall 16 is substantially impermeable to the passage of drug 19. In FIG. 4 wall 16 comprises (a) an aqueous emulsion of ethylacrylatemethyl methacrylate, a 70/30% copolymer having a molecular weight of about 800,000 and a glass transition temperature of about 10° C., and (b) an aqueous latex of ethyl cellulose having a particle size of 0.1 to 0.3 microns average.

Figure 5:
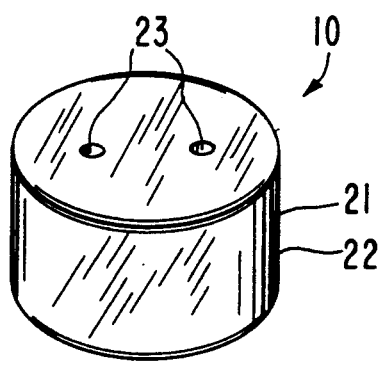
FIG. 5 is a view of the osmotic device of FIG. 3 in opened section illustrating the osmotic device comprising another embodiment of the wall-forming coating composition provided by the invention.

In FIG. 5 another embodiment of dosage form 10 is illustrated made as an osmotic drug delivery device 10. In FIG. 5 osmotic dosage form 10 comprises a body member 21 comprising a wall 22 that surrounds and forms an internal compartment, not seen in FIG. 5. Dosage form 10 comprises at least one or more passageways 23 formed during the manufacture of dosage form 10, or passageway 23 optionally is formed when dosage form 10 is in a fluid environment of use. Passageway 23 connects the interior of dosage form 10 with the exterior for delivering a drug to a biological environment of use.

Figure 6:
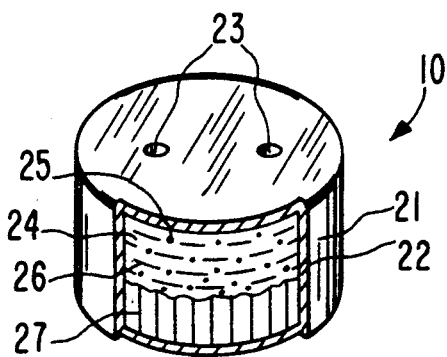
FIG. 6 is an open view of dosage FIG. 5 wherein FIG. 6 comprises a wall consisting of a three component composition.

In FIG. 6, dosage form 10 is an opened view of dosage form 10 of FIG. 5. In FIG. 6 dosage form 10 comprises body member 21, aqueous coated annealed wall 22 and exit ports 23. Wall 22 surrounds and forms an internal compartment 24. Internal compartment 24 comprises a first composition comprising a drug identified by dots 25, and an optional osmagent or optional dispensable osmopolymer identified by dashes 26. Compartment 24 comprises a second composition identified by vertical lines 27, comprising an expandable hydrogel. First composition 25 and second composition 27 are in laminar arrangement, and they cooperate with wall 22 for the effective delivery of drug 25 through exit passageway 23. In FIG. 6, wall 22 is a three component composition comprising (a) an aqueous emulsion of ethylacrylate methyl methacrylate, (b) an aqueous latex of ethyl cellulose and (c) a hydrophilic polymer such as polyvinyl alcohol.

While FIGS. 1 through 6 illustrate various embodiments of dosage form 10 that can be coated with the coatings of this invention, it is to be understood the coating composition can be applied to a wide variety of dosage forms that have various shapes and sizes. The coating composition can be applied to devices including buccal, implant, artificial gland, cervical, intrauterine, nasal, vaginal, anal-rectal, osmotic, diffusion, elastomeric, and the like. In these forms the dosage form is coated with the coat of the invention and it can be adapted for administering a beneficial medicine to animals, warm-blooded mammals, humans, farm and zoo animals, avians, reptiles, and the like.

DETAILED DESCRIPTION OF THE INVENTION

In accordance with the practice of this invention a drug, or a drug delivery device, is provided by coating or forming a wall with the coating composition provided by this invention. The coating composition comprises an aqueous emulsion of an alkyl-acrylate-alkyl methacrylate. This aqueous synthetic polymer emulsion is made by emulsion polymerization. In an emulsion polymerization process the monomers are finely distributed by the addition of an emulsifier in water. The emulsifier accumulate at the boundary between the monomer droplets and the water, but they also form miscelles in the aqueous phase, in which the monomer molecules are solubilized. Before the start of the olymerization one milliliter of such an emulsion contains, in addition to the monomers in solution, about $10^{18}$ miscelles with solubilized monomers and $10^{18}$ monomer droplets stabilized by the emulsifier.

Polymerization is started by the addition of water soluble initiator, generally a radical initiator to be dissolved in the monomers reaction vessel first. The activated monomers or oligomers migrate into the miscelles and lead to the polymerization of the solubilized monomers. As a latex particle is formed from the miscelle, this particle then swells and takes up more monomer from the aqueous phase. Monomer molecules migrate from the monomer droplets through the water phase into the latex particles until all monomer droplets are dissolved and all the monomer is converted to macromolecules. In this process the latex particles gradually increase in size until the polymerization is complete. A milliliter of the final dispersion generally contains $10^{14}$ latex particles, each consisting of several hundred monomolecules. The macromolecules comprise $10^3$ to $10^4$ monomer structural units resulting in a molecular weight of $10^5$ to $10^6$. The emulsion comprises polyacrylates-methacrylates of the following structure:

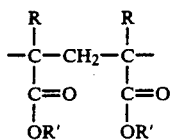

wherein R is the hydrogen or a lower alkyl of 1 to 7 carbons such as methyl, ethyl, and the like, and R' is a lower alkyl radical of 1 to 7 carbons such as methyl, ethyl, and the like. Procedures for manufacturing polyacrylate-methacrylate emulsions are described in *Drugs Made in Germany*, Vol. 16, No. 4, pp 126–36, (1973). The emulsions are commercially available as Eudragit ® from Rohm Pharma, Weiterstadt, West Germany, and from Rohm Tech, Inc., Malden, Mass. The emulsions are available as Eudragit ®-E30D, a copolymerization product based on polyacrylic and methacrylic acid esters, and as Eudragit ®-L30D a copolymerization product based on methacrylic and acrylic acid esters.

The coating composition comprises also an aqueous polymeric dispersion of ethyl cellulose. An aqueous emulsion comprising ethyl cellulose is prepared by a polymer emulsification process. The process comprises dispersing a liquified water insoluble polymer phase in an aqueous liquid medium phase containing at least one nonionic, anionic or cationic emulsifying agent in the presence of a compound selected from the group consisting of hydrocarbons, hydrocarbyl alcohols, ethers, alcohol esters, amines, halides and carboxylic acid esters that are inert, non-volatile, water insoluble, liquid and contain a terminal aliphatic hydrocarbyl group of at least 8 carbons, and mixtures thereof, and subjecting the resulting emulsion to a comminuting force sufficient to enable the production of an aqueous emulsion containing polymer particles averaging less than about 0.5 micron in size.

An aqueous latex of ethyl cellulose having a 0.1 to 0.3 micron particle size is prepared as follows: first, sodium lauryl sulfate and cetyl alcohol are dissolved in deionized water. Then a solution of ethyl cellulose comprising ethyl cellulose in toluene-methyl alcohol-methylene chloride is added to the sodium lauryl sulfate-cetyl alcohol water phase to form an emulsion. The emulsion is next homogenized by passing it through a submicron dispenser operated at about 6000 psi. The homogenized emulsion next is placed into a rotating flask and the solvents evaporated by slowly rotating the flask at about 50° C. and at 100 mmHg vacuum to remove all the solvent and to concentrate the polymer emulsion. The evaporation is continued for about three hours to provide a stable ethyl cellulose latex comprising 18% solids. Procedures for preparing ethyl cellulose emulsions are disclosed in U.S. Pat. No. 4,177,177. Emulsions comprising ethyl cellulose are commercially available from FMC Corporation, Philadelphia, Pa.

The coating composition provided by the invention also comprises a hydrophilic polymer. Representative polymers include polyvinyl alcohol that is 99% hydrolyzed and has a molecular weight of about 100,000; polyvinyl pyrrolidone having a molecular weight of about 100,000 to 360,000; hydroxypropylmethylcellulose having a molecular weight of 9,200 to 5,000,000; hydroxypropylcellulose, acidic carboxy polymers having a molecular weight of 450,000 to 4,000,000; polyethylene oxide having a molecular weight of 100,000 to 5,000,000, and the like.

The coating composition provided by the invention generally comprises (a) about 10 to 60 weight percent (wt %) of an aqueous emulsion of the alkylacrylate methacrylate, (b) from 10 to 60 wt % of the aqueous emulsion of ethyl cellulose and, optionally, (c) from 0 to 60 wt % of a hydrophilic polymer, with the amount of all ingredients equal to 100 wt %. For example, in more specific embodiments a coating composition comprises (d) 40 wt % of an aqueous emulsion of ethylacrylate methyl methacrylate wherein the monomers are present in a 70/30 ratio in the copolymer, 40 wt % of an aqueous emulsion of ethyl cellulose, and 20 wt % of polyvinyl pyrrolidone; a coating comprising (e) 36 wt % of the emulsion of ethylacrylate methyl methacrylate, 24 wt % of the emulsion of ethyl cellulose and 40 wt % of hydroxypropylmethylcellulose exhibiting a molecular weight of 9,200; a coating composition comprising (f) 36 wt % of the emulsion of ethylacrylate methyl methacrylate, 24 wt % of the aqueous emulsion of ethyl cellulose, and 40 wt % polyethylene oxide having a molecular weight of about 50,000; a composition comprising (g) 31 wt % of an aqueous emulsion of methylacrylate ethyl methacrylate, 29 wt % of an aqueous emulsion of ethyl cellulose and 40 wt % of an acidic carboxyvinyl polymer; and a compostion comprising (h) 36 wt % of an aqueous emulsion of ethylacrylate methyl methacrylate, 24 wt % of an aqueous emulsion of ethylcellulose and 40 wt % of polyvinyl alcohol having a molecular weight of 4,000,000.

The coating composition can be applied to a drug or to a compressed drug core by standard manufacturing procedures. For example, one manufacturing procedure that can be used for coating a drug substrate is the air suspension technique. The air suspension technique consists in suspending and tumbling a drug, or a compressed drug core to be coated, in a current of air comprising the coating composition until a coat is applied to the drug or to the drug core. The air suspension procedure is known in U.S. Pat. No. 3,207,824; in *J. Am. Pharm. Assoc.*, Vol. 48, pp 451–59, (1959); and in ibid, Vol. 49, pp 82–84, (1960). A drug or a drug core can be coated or surrounded with the wall forming composition in a Wurster ® air suspension coater, or in an Aeromatic ® air suspension coater. Other coating procedures such as pan coating can be used for applying the coat. Generally the coat that surrounds a drug, or a drug core, will have a thickness of 1 to 25 mils, usually 4 to 12 mils thick.

The drug coated product generally is annealed or cured at a temperature of about 35° C. to 65° C., usually for 24 to 72 hours. More specifically, in a preferred embodiment, the coated manufacture is dried at 50° C. for 30 hours in a forced air oven to yield the final product.

The expression, "exit passageway," as used in FIGS. 3 through 6, for a drug delivery device comprising a coated composition as provided by this invention, denotes means and methods suitable for the controlled, metered release of a drug from a drug delivery device or from a drug dosage form. The exit means comprises at least one passageway, orifice, or the like, through the coated wall of a dosage form. The expression, "at least one passageway," embraces aperture, orifice, bore, pore, porous element, through which pores a drug can travel, a hollow fiber, capillary tube, porous overlay, porous insert, and the like. The expression also includes a material that erodes or is leached from a wall in a fluid environment of use to produce at least one passageway of controlled releasing dimensions. Representative materials for forming a passageway or two passageways, or a multiplicity of passageways in an environment of use, include an erodible innocuous poly(glycolic acid), or poly(lactic acid) member in the wall, a gelatinous filament, a particle of polyvinyl alcohol leachable materials such as fluid removable pore forming polysaccharide, salt, oxide, polyhydric alcohol, and the like. A passageway or a plurality of passageways of governed dimensions for the controlled release of drug can be formed by leaching a passageway forming material, such as sorbitol, from the wall. The passageway can have any shape such as round, triangular, square, elliptical, irregular, and the like, for assisting in the metered release of a drug from a dosage form. A dosage form can comprise one or more than one passageway in spaced apart relations which are, optionally, on more than a single surface of a dosage form. The passageways and equipment for forming a passageway are disclosed in U.S. Pat. Nos. 3,845,770; 3,916,889; 4,063,064; and in 4,088,864. Representative passageways formed by the governed leaching of a pore former to produce a pore of precontrolled rate releasing size are disclosed in U.S. Pat. Nos. 4,200,098 and 4,285,987.

The expression, "therapeutically active drug," as used herein, denotes a beneficial medicine neat, or a composition comprising a beneficial drug. In the specification and in the accompanying claims, the term, "medicine and drug," are used as equivalents, and these terms include any physiologically or pharmacologically active substance that produces a local or a systemic effect in animals, including warm-blooded mammals, primates and humans. The terms, "physiologically and pharmacologically," are defined in *Stedman's Medical Dictionary*, (1966), published by Williams and Wilkins, Baltimore, Md. The active drug that can be coated, or the drug that can be placed into a drug delivery device coated with the composition of this invention, comprise inorganic and organic drugs that include, without limitation, drugs that act on the central nervous system, depressants, hypnotics, sedatives, psychic energizers, tranquilizers, anticonvulsants, muscle relaxants, anti-Parkinsons, analgesics, anti-inflammatories, local anesthetics, muscle contractants, anti-microbials, anti-malarials, hormones, contraceptives, sympathomimetics, diuretics, paraciticides, neoplastics, hypoglycemics, ophthalmics, electrolytes and cardiovascular drugs. These drugs and the daily dosage is known to the art in *Pharmaceutical Sciences*, edited by Remington, 16th Ed., (1980), published by Mack Publishing Company, Easton, Pa.

The drug can be in various pharmaceutically acceptable forms, such as uncharged molecules, molecular complexes, pharmacologically acceptable salts such as hydrochloride, hydrobromide, sulfate, laurylate, palmitate, phosphate, nitrate, borate, acetate, maleate, tartrate, oleate and salicylate; for acidic medicines such as salts of metals, amines or organic cations, for example quaternary ammonium can be used. Derivatives of medicine such as an ester, ether and amides can be used for the purpose of this invention. Also, a medicine that is water insoluble can be used in a form that is a water soluble derivative thereof to serve as a solute, and on its release from a dosage form it is converted by enzymes, hydrolyzed by the body pH, or by other metabolic process, to the originally biologically active form.

The osmopolymer 27 used for making the osmotic device of FIG. 6 comprises a homopolymer that exhibits an osmotic pressure gradient across a fluid permeable wall, imbibes fluid into dosage form 10, expands and pushes drug 25 through passageway 23 to the exterior of device 10. The osmopolymers are hydrophilic polymers comprising noncross-linked hydrogels and lightly cross-linked hydrogels, such as cross-linked by covalent or ionic bonds. The hydrophilic hydrogels usually exhibit a 2 to 50 fold volume increase comprising acidic carboxy polymers having a molecular weight of 450,000 to 4,000,000; poly(hydroxyalkyl methacrylate) polymers having a molecular weight of 30,000 to 5,000,000; poly(vinylpyrrolidone) having a molecular weight of 10,000 to 360,000; polyacrylic acid having a molecular weight of 80,000 to 200,000; polyethylene oxide polymers having a molecular weight of 100,000 to 5,000,000, and the like. Representative polymers that form hydrogels are known to the prior art in U.S. Pat. Nos. 3,865,108 issued to Hartop; 4,002,173 issued to Manning; 4,207,893 issued to Michaels; 4,327,725 issued to Cortese et al, and in *Handbook of Common Polymers*, by Scott and Roff, published by Chemical Rubber Company, Cleveland, Ohio.

Osmagent 20 as seen in FIG. 4, and osmagent 26 as seen in FIG. 6, are osmotically effective compounds that exhibit an osmotic pressure gradient across a wall against a fluid. Osmagents are known also as osmotically effective solutes. Representative osmagents include magnesium sulfate, magnesium chloride, sodium chloride, lithium chloride, potassium sulfate, sodium sulfate, lithium sulfate, potassium chloride, sodium sulfate, mannitol, urea, sorbitol, inositol, raffinose, sucrose, glycose, and the like. The osmagents are known in U.S. Pat. No. 4,327,725.

DETAILED DESCRIPTION OF THE EXAMPLES

The following examples are merely illustrative of the present invention and they should not be considered as limiting the scope of the invention in any way, as these examples and other equivalents thereof will become more apparent to those skilled in the drug delivery art in the light of the present disclosure, the drawings and the accompanying claims.

EXAMPLE 1

A drug delivery dosage form adapted, designed and shaped as an osmotic delivery system is manufactured as follows: first, 98.7 wt % potassium chloride, 1.2 wt % silicon dioxide and 0.1 wt % stearic acid are added to a blender to produce a homogeneous blend. Then the blend is compressed into potassium chloride drug cores.

The drug cores are coated with an aqueous emulsion. The cores weigh 500 mg and they are added to an Aeromatic coater. The coating composition comprises 36 wt % of aqueous emulsion ethylacrylate methyl methacrylate copolymer, 24 wt % aqueous emulsion of ethyl cellulose and 40 wt % polyvinyl alcohol.

The aqueous emulsion coat is applied in an Aeromatic air suspension coater at a process air temperature of 42° C., an atomizing air pressure of 2.4 atm, a coating solution pumping rate of 15 milliliters per minute, and possessing a solid content of copolymer of about 10 wt %.

The coated systems next were cured in a forced air oven for 30 hours at 50° C. The systems were cooled to room temperature and a 0.037 mm exit port was laser drilled through the dry coated wall that surrounds the core of potassium chloride.

EXAMPLE 2

An emulsion coat is prepared by taking (a) 40 wt % methylacrylate ethyl methacrylate copolymer, pigment, lactose and water and blending with (b) 40 wt % ethyl cellulose, sodium lauryl sulfate and water, and blending all ingredients with 20 wt % polyvinyl alcohol with vigorous stirring for 40 minutes to yield the blended emulsion. The emulsion is applied as an external wall to a drug core for providing osmotic dosage forms.

The osmotic dosage forms are manufactured for oral administration and comprise the following: a first composition is prepared by passing through a 40 mesh screen 74.40 wt % polyethylene oxide having a molecular weight of 200,000. Then 20.10 wt % of nifedipine and 5.00 wt % of hydroxypropylmethylcellulose having an average molecular weight of 11,200 is added to the polyethylene oxide and the three ingredients mixed for about 10 minutes in a conventional mixer. While the three ingredients are mixing, 300 ml of denatured anhydrous ethanol is added slowly to the mixer and the mixing continued for an additional five minutes. The wet granulation is passed through a 20 mesh screen, dried at room temperature for 16 hours and passed again through a 20 mesh screen. Finally, 1.5 wt % of magnesium stearate is added to the granulation and all the ingredients mixed on a roller mill for one to three minutes.

A second composition is prepared by mixing 64.30 wt % of polyethylene oxide having a molecular weight of 5,000,000 with 29.20 wt % sodium chloride and the mix passed through a 40 mesh screen. The just prepared mixture is mixed with 5.00 wt % hydroxypropylmethylcellulose having a number average molecular weight of 9,200 and with 1.00 wt % of ferric oxide for 10 minutes in the mixer. Then, 300 ml of denatured anhydrous ethanol is added slowly to the blending mixture and all the ingredients mixed for an additional five minutes. The freshly prepared wet granulation is passed through a 20 mesh screen, allowed to dry at room temperature for 16 hours, and again passed through a 20 mesh screen. The screened granulation is mixed with 0.50 wt % magnesium stearate in a roller mill for 10 minutes.

A drug core is prepared by adding 328 mg of the first composition to a tablet press and tamped, then 164 mg of the second composition is added to the press and the two compositions pressed into a two-layered drug core. The compressed two-layered drug core is coated with a coating composition and the coat cured with the aid of heat as described in Example 1. Finally, a 20 mil orifice is drilled through the coated wall to provide the final dosage form.

EXAMPLE 3

An emulsion coat is prepared by blending 60 wt % of an aqueous emulsion of ethyl acrylate methyl methacrylate titanium, lactose and water, known also as Eudragit ®-E30D, with 40% of an aqueous emulsion of ethyl cellulose, dibutyl sebacate, hydroxypropylmethylcellulose and water, also known as Aquacoat ® coat, to produce a uniform homogeneous emulsion.

Next, a drug core weighing 323.23 mg is prepared comprising 5.96 wt % salbutamol hemisulfate, 89.01 wt % sodium chloride, 20 wt % polyvinyl pyrrolidone, 2 wt % cross-linked sodium carboxymethylcellulose and 1.0 wt % magnesium stearate. The drug core is coated with the emulsion, annealed, and a 20 mil passageway drilled through the freshly prepared wall of the dosage form to provide an osmotic delivery device.

An embodiment of the invention pertains to a method for administering a drug to the gastrointestinal tract to establish a drug blood level. The method comprises the steps of: (A) admitting into the gastrointestinal tract an osmotic dosage form comprising: (1) a wall comprising a non-toxic emulsion that is permeable to the passage of fluid and substantially impermeable to the passage of drug, which wall forms: (2) a compartment comprising a gastrointestinal administrable drug; and (3) at least one exit passageway in the emulsion-based wall that connects the exterior of the dosage form with the interior of the dosage form; (B) imbibing fluid through the wall into the compartment at a rate determined by the permeability of the wall and the osmotic pressure gradient across the wall to form, in the compartment, a dispensable composition that is hydrodynamically and osmotically pumped through the passageway from the dosage form; (C) thereby delivering the drug in a therapeutically effective amount to the gastrointestinal tract for passing into the blood circulation for established a blood level over a prolonged period of time from 4 hours to 24 hours.

The invention pertains to an dosage form comprising an emulsion coat or wall for delivering a drug at a controlled rate over time. While there has been described and pointed out the novel features of the invention as applied to presently preferred embodiments, those skilled in the art will appreciate that various modifications, changes and omissions in the invention disclosed and claimed can be made without departing from the spirit of the invention.

We claim:
1. An osmotic device comprising:
   (a) a wall comprising an aqueous emulsion of a lower alkylacrylate-lower methacrylate wherein the lower alkyl comprises 1 to 7 carbon atoms and an aqueous emulsion of ethyl cellulose, said wall formed by calescence at a temperature up to 65° C. for up to 72 hours, which wall surrounds;
   (b) a compartment;
   (c) a therapeutically effective amount of drug in the compartment; and,
   (d) at least one passageway in the wall connecting the exterior with the interior of the device for delivering drug over time.
2. The osmotic device according to claim 1, wherein the emulsion comprises a hydrophilic polymer.
3. THe osmotic device according to claim 1, wherein the drug is nifedipine.
4. The osmotic device according to claim 1, wherein the drug is salbutamol.

* * * * *

UNITED STATES PATENT AND TRADEMARK OFFICE
CERTIFICATE OF CORRECTION

PATENT NO. : 5,019,397
DATED : May 28, 1991
INVENTOR(S) : Patrick S.-L. WONG, Felix THEEUWES It is certified that error appears in the above-identified patent and that said Letters Patent is hereby corrected as shown below:

In the ABSTRACT, in the first sentence of the Abstract, after the word "emulsion", delete the word "that", so the first sentence reads:
----A dosage form is disclosed comprising a cured emulsion coat that surrounds a drug.----

In column 10, claim 1, in line 54, "calescence" should read ----coalescence----.

Signed and Sealed this

Fifteenth Day of September, 1992

Attest:

DOUGLAS B. COMER

Attesting Officer

Acting Commissioner of Patents and Trademarks